US00PP22152P2

(12) United States Plant Patent

Klemm et al.

(10) Patent No.: US PP22,152 P2

(45) Date of Patent: Sep. 13, 2011

(54) *CALIBRACHOA* PLANT NAMED 'KLECA09172'

(50) Latin Name: ***Calibrachoa* hybrid**
Varietal Denomination: KLECA09172

(75) Inventors: Nils Klemm, Stuttgart (DE); Anita Stoever, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/798,203

(22) Filed: Mar. 31, 2010

(51) Int. Cl.
*A01H 5/00* (2006.01)

(52) U.S. Cl. ..... Plt./413

(58) Field of Classification Search ..... Plt./263, Plt./413

See application file for complete search history.

*Primary Examiner* — Susan McCormick Ewoldt

(74) *Attorney, Agent, or Firm* — Jondle & Associates, P.C.

(57) ABSTRACT

A new *Calibrachoa* plant named 'KLECA09172' particularly distinguished by red flower color, an early flowering time, an upright to cascading growth habit, and a uniformly mounded plant habit, is disclosed.

1 Drawing Sheet

Genus and species: *Calibrachoa* hybrid.
Variety denomination: 'KLECA09172'.

BACKGROUND OF THE NEW PLANT

The present invention comprises a new and distinct variety of *Calibrachoa,* botanically known as *Calibrachoa* hybrid and hereinafter referred to by the variety name 'KLECA09172'. The new variety was discovered as a seedling resulting from a cross conducted in June 2005 in Stuttgart, Germany. The female parent was the proprietary *Calibrachoa* plant 'X 456' (unpatented), while the male parent was the proprietary *Calibrachoa* plant 'X 170' (unpatented).

The new variety was first propagated via vegetative cuttings in May 2006 in Stuttgart, Germany and has been asexually reproduced by vegetative propagation cuttings and in-vitro propagation in Stuttgart, Germany for more than 60 generations. The present invention has been found to retain its distinctive characteristics through successive asexual propagations via vegetative cuttings.

'KLECA09172' has not been made publicly available or sold more than one year prior to the filing date of this application.

SUMMARY OF THE INVENTION

The following are the most outstanding and distinguishing characteristics of this new variety when grown under normal horticultural practices in Stuttgart, Germany.

1. Red flower color;
2. An early flowering time;
3. An upright to cascading growth habit; and
4. A uniformly mounded plant habit.

DESCRIPTION OF THE PHOTOGRAPH

This new *Calibrachoa* plant is illustrated by the accompanying photograph which shows flowers and foliage of the plant. The colors shown are as true as can be reasonably obtained by conventional photographic procedures. The photograph was taken in May 2009 of a 5-month old *Calibrachoa* plant, grown in a glass greenhouse in Stuttgart, Germany.

DESCRIPTION OF THE NEW VARIETY

The following detailed descriptions set forth the distinctive characteristics of 'KLECA09172'. The data which defines these characteristics were collected from asexual reproductions carried out in Stuttgart, Germany. The plant history was taken in May 2009 on 5-month old plants which were planted as rooted cuttings in 11 centimeter pots and then grown in a glass greenhouse. The plants had one terminal pinch after potting. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Solanaceae.
- *Botanical.*—*Calibrachoa* sp.
- *Common.*—*Calibrachoa* Hybrida.

Parentage:
- *Female.*—The proprietary *Calibrachoa* plant 'X 456' (unpatented).
- *Male.*—The proprietary *Calibrachoa* plant 'X 170' (unpatented).

Growth:
- *Form.*—Uniformly mounded.
- *Habit.*—Upright to cascading.
- *Height* (*measured from the top of the soil*).—8.0 cm.
- *Width* (*horizontal plant diameter*).—16.0 cm.
- *Time to produce a finished flowering plant.*—9 weeks.
- *Outdoor plant performance.*—Continuously flowering, healthy.
- *Time to initiate and develop roots.*—21 days.
- *Root description.*—Fine, fibrous, freely branching, moderate density, white roots.

Stems:

*Length of basal branches.*—8.0 cm.

*Internode length.*—2.0 cm.

*Diameter of branches* (*from midpoint*).—6.0 cm to 9.0 cm.

*Stem color.*—RHS 144B.

*Texture.*—Smooth.

*Anthocyanin.*—Absent.

*Pedicel.*—Color: RHS 144C. Length: 2.5 cm. Diameter: 0.1 cm. Texture: Smooth.

Leaves:

*Arrangement.*—Alternate, simple, sessile.

*Size.*—Length: 3.0 cm. Width: 0.8 cm.

*Shape.*—Lanceolate to elliptic.

*Apex.*—Obtuse to slightly acute.

*Base.*—Attenuate.

*Margin.*—Entire.

*Color* (*both immature and mature leaves*): Upper surface: RHS 147B. Lower surface: RHS 146B.

*Texture.*—Smooth.

*Venation pattern.*—Pinnate.

*Venation color.*—RHS 146D.

*Petioles.*—Absent, sessile.

Flower bud:

*Shape.*—Irregular to oblong.

*Size.*—Length: 2.0 cm. Diameter: 0.8 cm.

*Color at tight bud.*—RHS 64A.

Inflorescence:

*Blooming habit.*—Flowers face upright, single, axillary.

*Inflorescence type.*—Determinate inflorescence.

*Floret type.*—Single flowers.

*Lastingness of individual blooms on the plant.*—5 days.

*Fragrance.*—Absent.

Flowers:

*Immature flower.*—Diameter: Horizontal: 2.3 cm. Vertical: 2.3 cm. Color: Upper surface: RHS 46B. Lower surface: RHS 63B.

*Mature flower.*—Diameter: Horizontal: 3.0 cm. Vertical: 2.6 cm. Color: Upper surface: RHS 46A. Lower surface: RHS 63A.

*Corolla tube.*—Color inside: RHS 14B. Color outside: RHS 14C. Tube length: 1.5 cm. Texture (both outside and inside): Smooth.

*Petals.*—Apex: Obverse. Base: Open, fused into the tube. Margin: Entire. Waviness of petals: Very weak. Lobation: Weak. Texture (both upper and lower surfaces): Smooth.

*Sepals.*—Calyx (composition): Actinomorphic. Shape: Lanceolate to elliptic. Apex: Acute. Base: Open, tube fused into the base. Margin: Entire. Length: 1.5 cm. Width: 0.2 cm. Color: Upper surface: RHS 144A. Lower surface: RHS 144B. Texture (both upper and lower surfaces): Smooth.

Reproductive organs:

*Stamens.*—Number: 5. Filament color: RHS 154C. Filament length: 0.6 cm to 0.9 cm. Filament diameter: 0.1 cm. Pollen color: RHS 7A. Pollen quantity: Moderate.

*Pistils.*—Number: 1. Length: 0.9 cm. Diameter: 0.1 cm. Stigma color: RHS 145A.

*Style color.*—RHS 145B.

Fruit and seed set: No fruit and seed set observed.

Disease and insect resistance: No particular resistance or susceptibility has been observed.

COMPARISON WITH PARENTAL AND COMMERCIAL VARIETYS

'KLECA09172' differs from the female parent *Calibrachoa* plant 'X 456' (unpatented), in that 'KLECA09172' has red flowers, whereas 'X 456' has dark-red to black-red flowers.

'KLECA09172' differs from the male parent *Calibrachoa* plant 'X 170' in that 'KLECA09172' has red flowers, whereas 'X 170' has pink-red flowers.

We claim:

1. A new and distinct variety of *Calibrachoa* plant named 'KLECA09172' as shown and described herein.

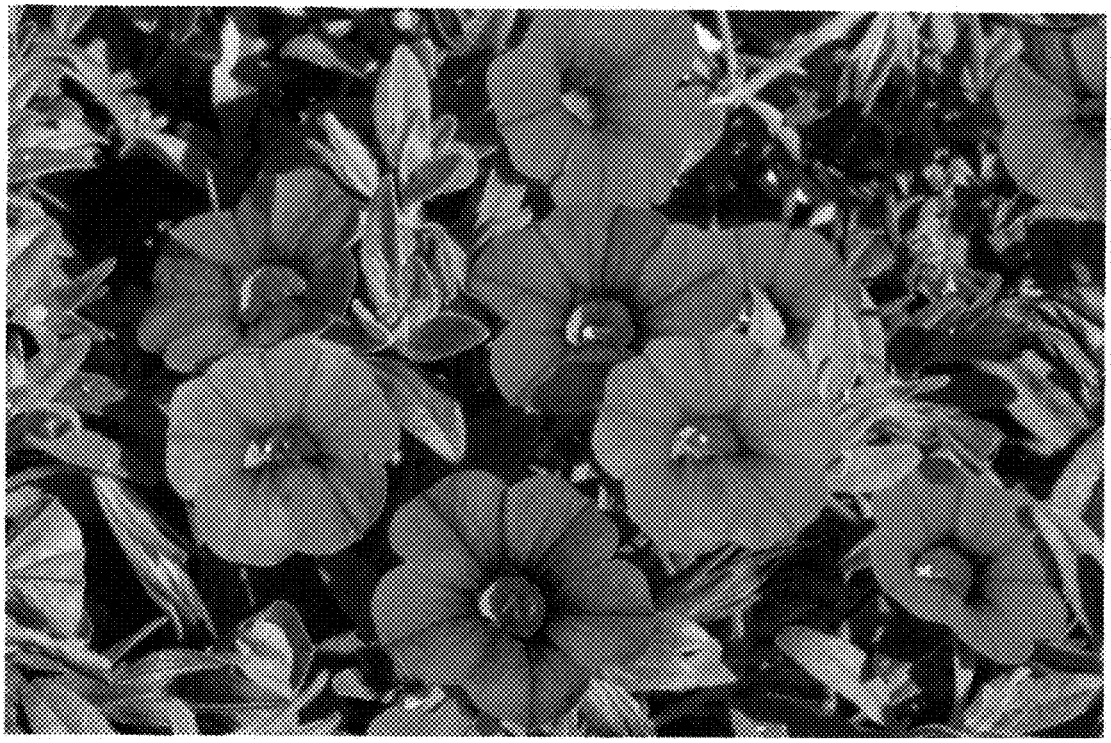

* * * * *